(12) United States Patent
Sethna et al.

(10) Patent No.: US 11,058,566 B2
(45) Date of Patent: Jul. 13, 2021

(54) VARIABLE RATE PROSTHESIS DELIVERY SYSTEM PROVIDING PROSTHESIS ALTERATIONS

(71) Applicant: Medtronic Vascular, Inc., Santa Rosa, CA (US)

(72) Inventors: Sohrab Sethna, Santa Rosa, CA (US); Jeffery Argentine, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 477 days.

(21) Appl. No.: 15/950,914

(22) Filed: Apr. 11, 2018

(65) Prior Publication Data

US 2019/0314178 A1 Oct. 17, 2019

(51) Int. Cl.
*A61F 2/966* (2013.01)

(52) U.S. Cl.
CPC ...... *A61F 2/966* (2013.01); *A61F 2210/0014* (2013.01)

(58) Field of Classification Search
CPC ........ A61F 2/966; A61F 2/9517; A61F 2/962; A61F 2/2436; A61F 2/95
See application file for complete search history.

(56) References Cited

U.S. PATENT DOCUMENTS

| | | |
|---|---|---|
| 7,935,141 B2 | 5/2011 | Randall et al. |
| 8,523,064 B1 | 9/2013 | Buchheit et al. |
| 8,585,750 B2 | 11/2013 | Argentine |
| 8,747,448 B2 | 6/2014 | Argentine |
| 9,445,928 B2 | 9/2016 | Argentine |
| 9,486,350 B2 | 11/2016 | Argentine |
| 2002/0111666 A1 | 8/2002 | Hart et al. |
| 2004/0127912 A1 | 7/2004 | Rabkin et al. |
| 2009/0018553 A1 | 1/2009 | McLean et al. |
| 2009/0099638 A1 | 4/2009 | Grewe |
| 2010/0036472 A1 | 2/2010 | Papp |
| 2010/0168756 A1 | 7/2010 | Dorn et al. |
| 2010/0174290 A1 | 7/2010 | Wuebbeling et al. |
| 2011/0282425 A1 | 11/2011 | Dwork |
| 2012/0053574 A1 | 3/2012 | Murray, III et al. |
| 2013/0331925 A1 | 12/2013 | Roeder et al. |

(Continued)

FOREIGN PATENT DOCUMENTS

WO 2015038875 A1 3/2015

OTHER PUBLICATIONS

PCT/US2019/025501, The International Search Report and the Written Opinion, dated Jul. 5, 2019, 15pgs.

(Continued)

*Primary Examiner* — Katherine M Rodjom

(57) ABSTRACT

Devices, methods, and systems for prosthesis delivery to patient vasculature are provided. A prosthesis delivery device provided herein delivers a prosthesis to the vasculature of a patient and permits an operator to deploy the prosthesis using a single action mechanism to deploy the prosthesis at a standard deployment rate and a dual action mechanism to deploy the prosthesis at an accelerated deployment rate. Deploying the prosthesis at an accelerated deployment rate results in alterations to the deployed prosthesis structure because the prosthesis is deployed with increased axial compression that results in the prosthesis having increased radial force.

19 Claims, 9 Drawing Sheets

(56) References Cited

U.S. PATENT DOCUMENTS

| | | |
|---|---|---|
| 2014/0046428 A1* | 2/2014 | Cragg ................... A61F 2/966 623/1.12 |
| 2014/0046429 A1 | 2/2014 | Cragg et al. |
| 2015/0081000 A1* | 3/2015 | Hossainy ................. A61F 2/90 623/1.2 |
| 2015/0265445 A1 | 9/2015 | Weber et al. |
| 2015/0305902 A1 | 10/2015 | Argentine |
| 2016/0120677 A1 | 5/2016 | Heanue et al. |

OTHER PUBLICATIONS

U.S. Appl. No. 15/498,198, filed Apr. 26, 2017, Argentine, Jeffery.
U.S. Appl. No. 15/498,178, filed Apr. 26, 2017, Argentine, Jeffery et al.

\* cited by examiner

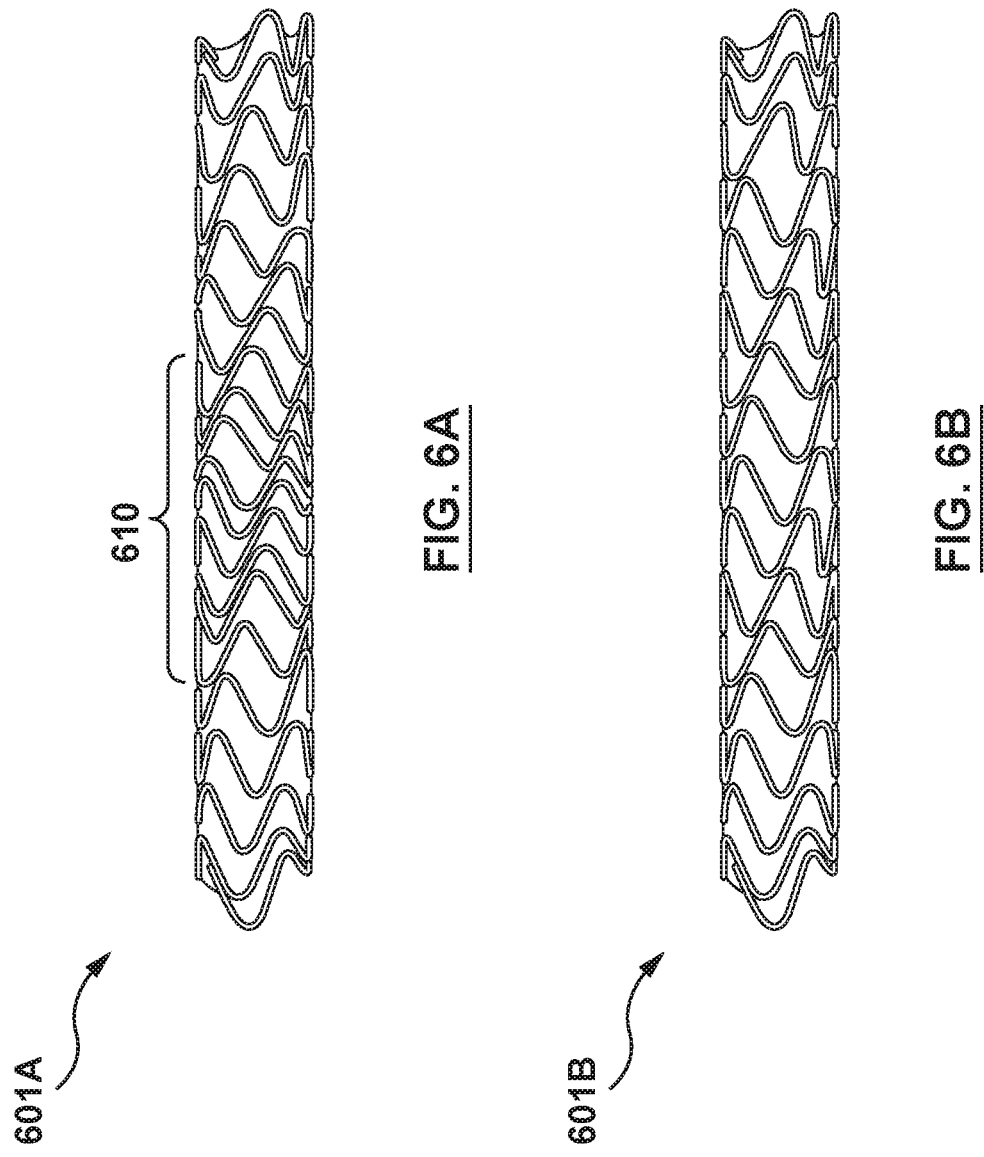

VARIABLE RATE PROSTHESIS DELIVERY SYSTEM PROVIDING PROSTHESIS ALTERATIONS

FIELD OF THE INVENTION

The present invention is related to prosthesis delivery systems and methods.

BACKGROUND

Prostheses for implantation in blood vessels or other similar organs of the living body are, in general, well known in the medical art. For example, prosthetic vascular grafts constructed of biocompatible materials have been employed to replace or bypass damaged or occluded natural blood vessels. In general, endovascular grafts typically include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. Thus, endovascular grafts are typically held in place by mechanical engagement and friction due to the opposition forces provided by the radially expandable stents. In another example, expandable stents may be deployed without the addition of a covering graft component.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life-threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as prostheses are preferably deployed through a less invasive intraluminal delivery procedure. More particularly, a lumen or vasculature is accessed percutaneously at a convenient and less traumatic entry point, and the prosthesis is routed through the vasculature to the site where the prosthesis is to be deployed. Intraluminal deployment is typically affected using a delivery catheter with coaxial inner and outer tubes arranged for relative axial movement. For example, a self-expanding prosthesis may be compressed and disposed within the distal end of an outer catheter tube distal of a stop fixed to the inner member. The catheter is then maneuvered, typically routed through a body lumen until the end of the catheter and the prosthesis are positioned at the intended treatment site. The stop on the inner member is then held stationary while the outer tube of the delivery catheter is withdrawn. The stop prevents the prosthesis from being withdrawn with the sheath. As the sheath is withdrawn, the prosthesis is released from the confines of the sheath and radially self-expands so that at least a portion of the prosthesis contacts and substantially conforms to a portion of the surrounding interior of the lumen, e.g., the blood vessel wall or anatomical conduit. The self-expanding stent structure may continue to provide radial force after deployment to maintain the patency of the graft within the blood vessel and to provide the force necessary to secure the graft in the deployment location.

In other examples, other types of stents, including uncovered stents, bare metal stents, and other stent structures, may be deployed in a similar procedure.

SUMMARY

Embodiments of the present invention relate generally to prosthesis delivery systems, and, more specifically, to prosthesis delivery systems and methods capable of deploying a prosthesis at multiple controlled deployment rates. Varying deployment rates may cause alterations to the structure of the deployed prosthesis, and an operator may use the disclosed devices and methods to achieve desired deployment results.

In an embodiment, a prosthesis delivery device is provided. The prosthesis delivery device includes a housing, an outer sheath including a proximal portion mechanically coupled to a sheath anchor within the housing, a pusher shaft having a distal portion disposed inside of the outer sheath and a proximal portion mechanically coupled to a pusher shaft anchor within the housing, a central shaft having a proximal portion and a distal portion disposed inside of the pusher shaft. The device further includes a first deployment assembly located exterior to the housing and configured to simultaneously advance the outer sheath and the pusher shaft in opposing axial directions, and a second deployment assembly located exterior to the housing configured to retract the outer sheath while maintaining the pusher shaft stationary relative to the housing.

In another embodiment, a method of delivering a prosthesis to a treatment site within the vasculature of a subject using a prosthesis delivery device is provided. The prosthesis delivery device includes at least an outer sheath, a pusher shaft, and a central shaft. The method includes delivering a prosthesis carrying tip of the prosthesis delivery device to the treatment site, retracting an outer sheath of the prosthesis delivery device to expose the prosthesis, simultaneous to retracting the outer sheath, advancing a pusher shaft of the prosthesis delivery device, a distal end of the pusher shaft contacting the prosthesis to advance the prosthesis distally along the central shaft, and retracting the outer sheath of the prosthesis delivery device to expose the prosthesis while maintaining a position of the pusher shaft.

In still another embodiment, a prosthesis delivery system is provided. A prosthesis delivery system includes a prosthesis configured for delivery to vasculature of a subject, a housing, an outer sheath including a proximal portion mechanically coupled to a sheath anchor within the housing, a pusher shaft having a distal portion disposed inside of the outer sheath and a proximal portion mechanically coupled to a pusher shaft anchor within the housing, and a central shaft having a proximal portion and a distal portion disposed inside of the pusher shaft, the prosthesis being mounted on the distal portion of the central shaft. The system further includes a first deployment assembly located exterior to the housing and configured to simultaneously advance the outer sheath and the pusher shaft in opposing axial directions, and a second deployment assembly located exterior to the housing configured to retract the outer sheath while maintaining the pusher shaft stationary relative to the housing.

BRIEF DESCRIPTION OF THE DRAWINGS

The accompanying figures, which are incorporated herein, form part of the specification and illustrate embodiments of a prosthesis delivery system. Together with the description, the figures further explain the principles of and enable a person skilled in the relevant art(s) to make, use, and implant the prosthesis described herein. In the drawings, like reference numbers indicate identical or functionally similar elements.

FIG. 6A illustrates an exemplary deployed prosthesis including an area of increased compression resulting from dual action deployment at an accelerated deployment rate.

FIG. 6B illustrates an exemplary deployed prosthesis having uniform distribution resulting from single action deployment at a standard deployment rate.

DETAILED DESCRIPTION OF THE INVENTION

Figure 1:
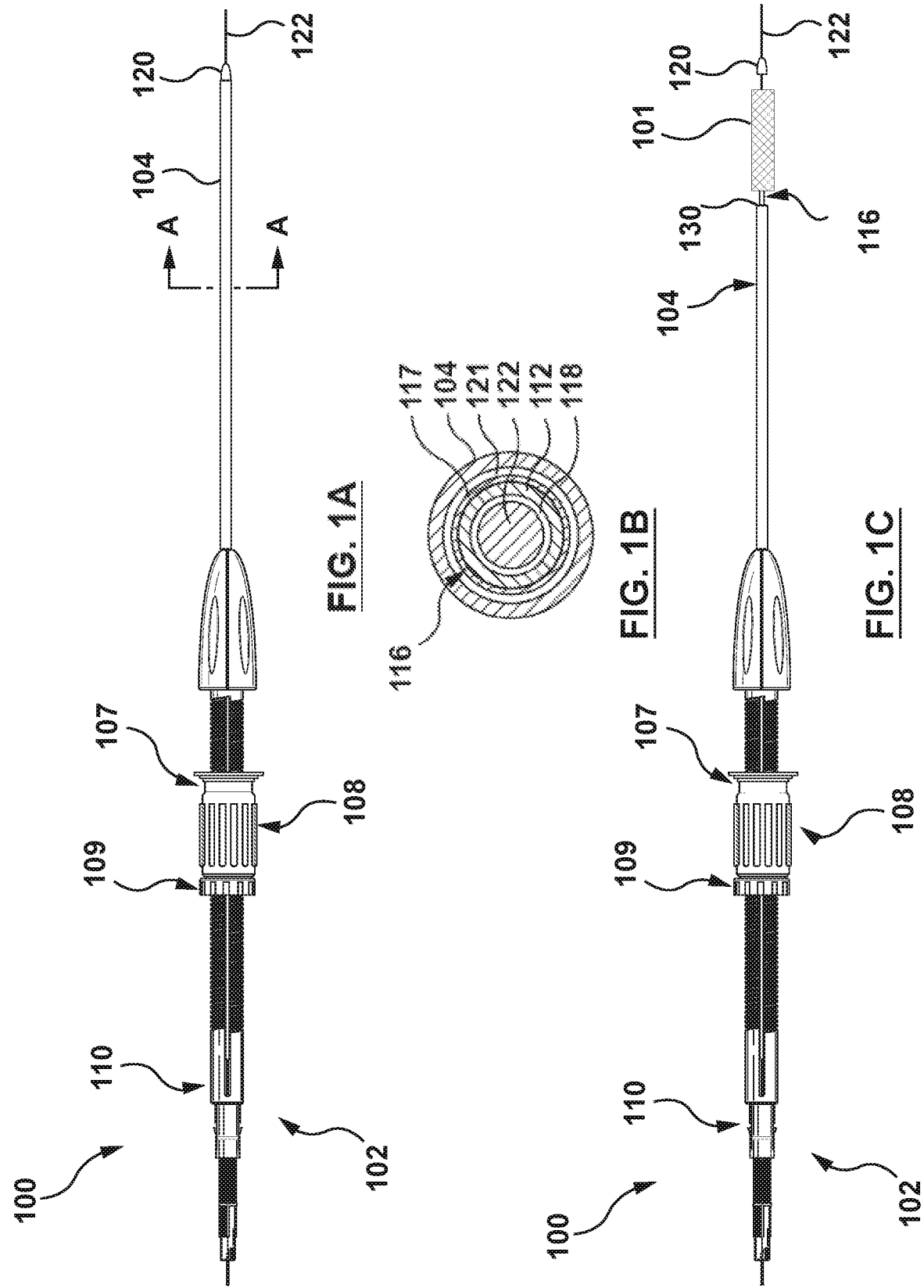
FIG. 1A is a view of a prosthesis delivery system according to aspects of this disclosure, wherein the prosthesis delivery system is in a delivery position.
FIG. 1B is a cross-sectional view of the prosthesis delivery system of FIG. 1A taken along line A-A of FIG. 1A.
FIG. 1C is a view of the prosthesis delivery system of FIG. 1A, wherein the prosthesis delivery system is in a deployed position.

Specific embodiments of the present invention are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the prosthesis "proximal" is the portion nearer the heart by way of blood flow path while "distal" is the portion of the prosthesis further from the heart by way of blood flow path. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive illustrative self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely illustrative in nature and is not intended to limit the invention or the application and uses of the invention. Although the description of the invention is in the context of treatment of blood vessels such as the aorta, coronary, carotid and renal arteries, the invention may also be used in any other body passageways where it is deemed useful. As another example, the description of the invention is in the context of deployment of prostheses. As used herein, "prosthesis" or "prostheses" may include any prosthesis including one or more stents or stent structures, including but not limited to stent-graft prostheses, uncovered stents, bare metal stents, drug eluting stents, and any other appropriate stent structure. Modifications can be made to the embodiments described herein without departing from the spirit and scope of the present invention. Therefore, the following detailed description is not meant to be limiting. Furthermore, there is no intention to be bound by any expressed or implied theory presented in the preceding technical field, background, summary or the following detailed description.

Embodiments hereof are directed to a delivery system for percutaneously delivering a prosthesis, the delivery system including a first deployment assembly (also referred to herein as a dual action deployment assembly) and a second deployment assembly (also referred to herein as a single action deployment assembly). A user may selectively deploy the prosthesis with a combination of the first and second deployment assemblies. More particularly, the single action deployment assembly deploys the prosthesis at a standard deployment rate. An outer sheath of the delivery system is retracted to expose the prosthesis and a pusher shaft prevents the prosthesis from retracting along with the outer sheath. The pusher shaft remains stationary when the single action deployment assembly is utilized for deploying the prosthesis. Conversely, the dual action deployment assembly deploys the prosthesis at an accelerated or faster deployment rate than the standard deployment rate. When the dual action deployment assembly is utilized for deploying the prosthesis, the outer sheath and the pusher shaft each move or translate in opposing axial directions with respect to one another. Stated another way, when the dual action deployment assembly is utilized for deploying the prosthesis, the outer sheath is proximally retracted to expose the prosthesis and the pusher shaft is simultaneously distally advanced to push the prosthesis into the patient vasculature. Deployment with the accelerated deployment rate of the first deployment assembly deploys the prosthesis with greater or increased axial compression relative to deployment with the single action deployment assembly. When the prosthesis is deployed with greater axial compression, the deployed prosthesis produces or exerts a greater radial force onto the surrounding vasculature as will be described in more detail herein. In an embodiment hereof, both the dual action deployment mechanism and the single action deployment mechanism are selectively operated during prosthesis deployment, thereby deploying the prosthesis with variable amounts of axial compression such that the deployed prosthesis has varying amounts of radial force.

More particularly, a delivery system 100 is shown in FIGS. 1A-1C. FIG. 1A is a side view of the delivery system 100, with an outer sheath 104 thereof shown in a delivery configuration in which the outer sheath 104 surrounds and constrains a prosthesis 101 (not shown in FIG. 1A) in a compressed or delivery configuration. FIG. 1B is a cross-sectional view taken along line A-A of FIG. 1A. FIG. 1C is a side view of the delivery system 100 after the outer sheath 104 has been retracted to allow the prosthesis 101 to self-expand to a deployed or expanded configuration. The delivery system 100 includes a handle 102 having a housing 110. The handle 102 includes a dual action deployment ring 109 (which is a component of a dual action deployment assembly 301 described in more detail below), a single action deployment ring 107 (which is a component of a single action deployment assembly 302 described in more detail below), and a grip barrel 108 that extends between the dual action deployment ring 109 and the single action deployment ring 107. Each of the dual action deployment ring 109, the grip barrel 108, and the single action deployment ring 107 are disposed exterior to, or on an exterior surface of, the housing 110. The components of the handle 102 will be described in detail herein with respect to FIGS. 3A-5B.

The delivery system 100 further includes an inner or central shaft 112 having a proximal portion and a distal portion, a pusher shaft 116 having a proximal portion and a distal portion, and the outer sheath 104 having a proximal portion and a distal portion. The outer sheath 104, the pusher shaft 116, and the central shaft 112 extend from within the housing 110 of handle 102. As best shown in FIG. 1B, the outer sheath 104 defines a lumen 121 and is slidingly and concentrically disposed over the pusher shaft 116. The pusher shaft 116 defines a lumen 117 and is slidingly and concentrically disposed over the central shaft 112. The pusher shaft 116 further includes a prosthesis contact surface 130 at a distal end thereof. The central shaft 112 defines a lumen 118 such that the delivery system 100 may be slidingly disposed and tracked over a guidewire 122. A tapered flexible nosecone or tip 120 may be coupled to the distal end of central shaft 112 as shown in FIG. 1A and FIG. 1C.

The prosthesis 101 is mounted over the central shaft 112 at a distal portion thereof and the outer sheath 104 surrounds and constrains the prosthesis 101 in a compressed or delivery configuration as shown in the side view of FIG. 1A. The prosthesis 101 is shown in the view of FIG. 1C but is obscured from view by the outer sheath 104 in FIG. 1A. The proximal ends of the outer sheath 104 and the pusher shaft 116 are operably coupled to the deployment assemblies of the handle 102, as described in greater detail below with respect to FIGS. 3A and 3B. During deployment of the prosthesis 101, the outer sheath 104 is proximally retracted with respect to the prostheses 101, thereby incrementally exposing the prosthesis 101. When the prosthesis 101 abuts against the prosthesis contact surface 130 of the pusher shaft 116, the pusher shaft 116 serves to maintain a longitudinal position of the prosthesis 101 with respect to the pusher shaft 116 to prevent the prosthesis 101 from retracting with the outer sheath 104 due to friction between the two components. When the delivery system 100 is properly positioned in situ, the outer sheath 104 is retracted to fully expose the prosthesis 101 and thereby permit full release of the prosthesis 101 from the delivery system 100. The deployed configuration of the prosthesis 101 is merely illustrative, and it would be apparent to one of ordinary skill in the art that the delivery system 100 may be utilized for delivering and deploying various types or configurations of self-expanding prostheses.

Figure 2:
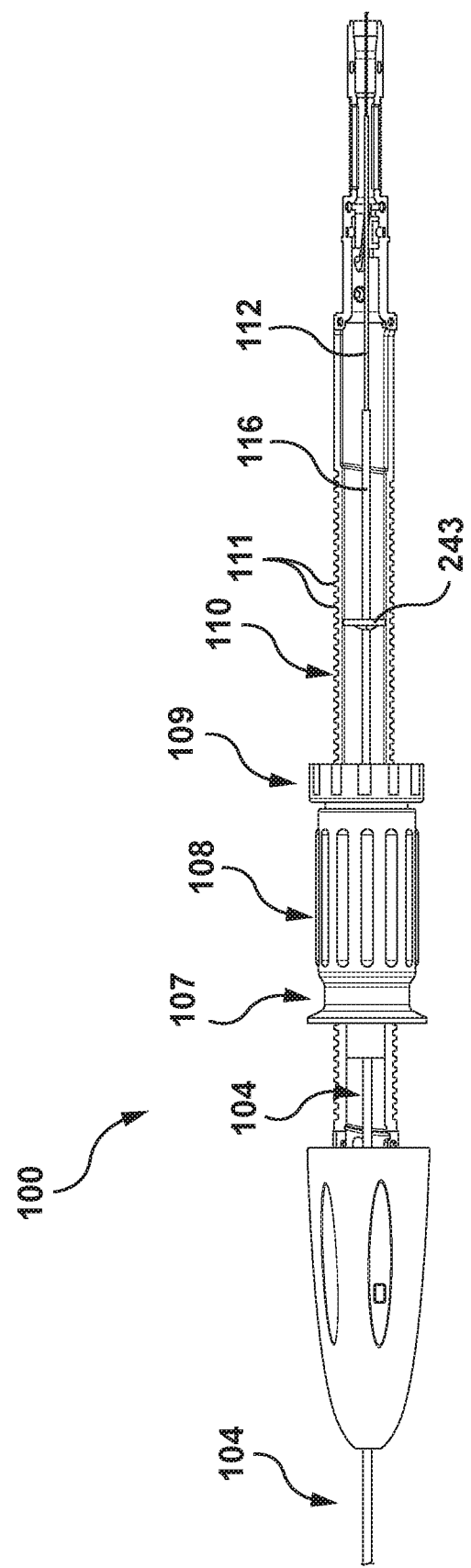
FIG. 2 illustrates the prosthesis delivery system of FIG. 1A with an enlarged cut-away view of a handle of the prosthesis delivery system.
Figure 3A:
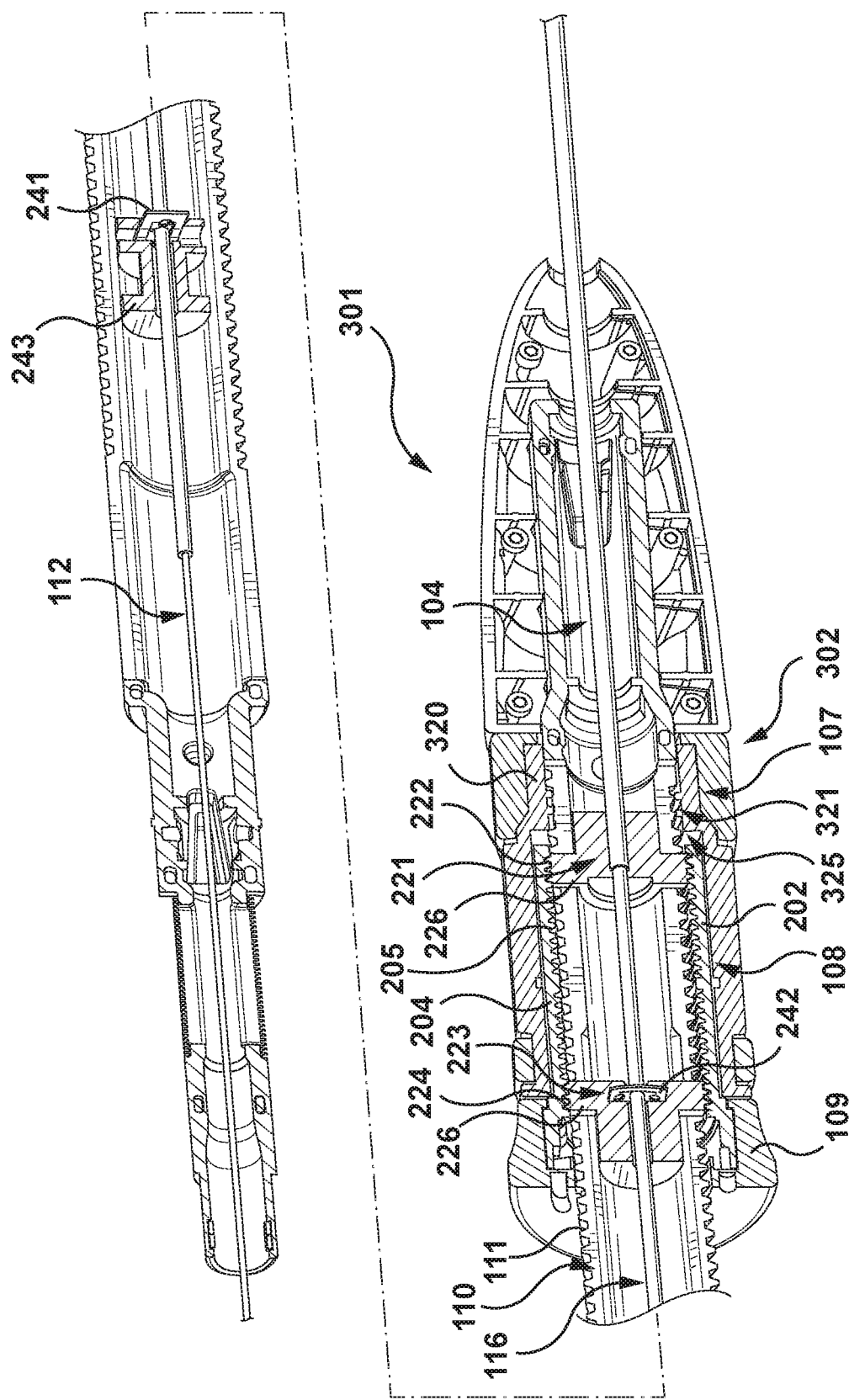
FIG. 3A is a sectional view of the handle of the prosthesis delivery system of FIG. 1A including a single action deployment mechanism and a dual action deployment mechanism.
Figure 3B:
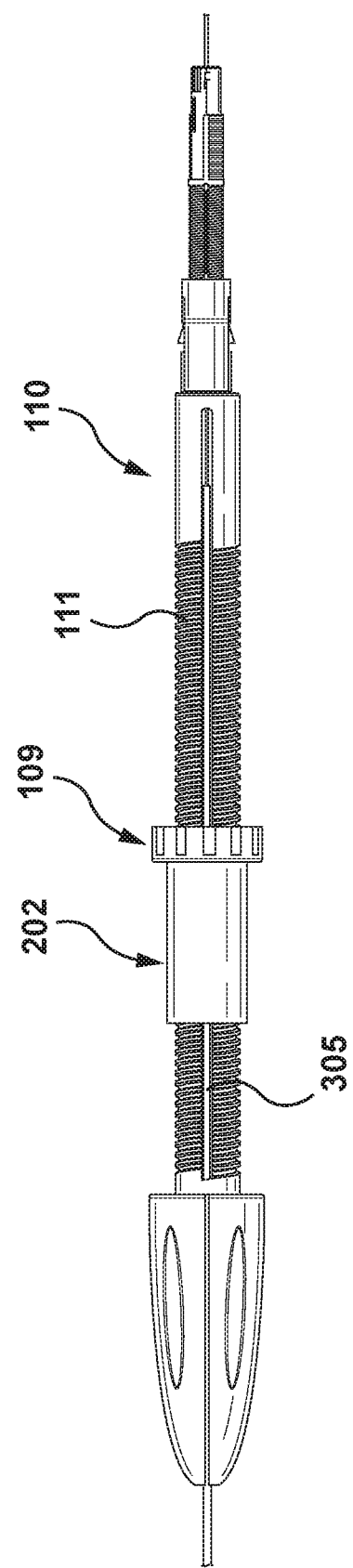
FIG. 3B is a plan view of a handle of the prosthesis delivery system of FIG. 1A.

Prior to a description of how each of the dual action deployment assembly 301 and the single dual action deployment assembly 302 operate, a structural description of the components of the delivery system 100 is required. FIG. 2 is an enlarged cut-away view of the handle 102. FIG. 3A illustrates a sectional view of the handle 102 of the delivery system 100 and provides a detailed view of the components of the dual action deployment assembly 301 and the components of the single action deployment assembly 302. FIG. 3B illustrates a plan view of the handle 102 of the delivery system 100 to illustrate the threaded exterior of the housing 110 and aspects of the dual action deployment assembly 301.

With primary reference to FIG. 3A, the delivery system 100 includes an outer sheath anchor 221 that is mechanically coupled and secured to a proximal portion of the outer sheath 104. The outer sheath anchor 221 is disposed within the housing 110. The outer sheath anchor 221 includes outer sheath anchor threads 222 which are arranged on thread extensions 226 thereof. The outer sheath anchor 221 is shaped and sized so as to comfortably fit inside the housing 110. In the embodiment depicted in FIG. 3A, the outer sheath anchor 221 is generally tubular or cylindrical with thread extensions 226 radially extending from opposing sides thereof as tabs. The outer sheath anchor 221 includes a central hole to permit the passage of the pusher shaft 116, the central shaft 112, and any other necessary components.

Figure 4A:
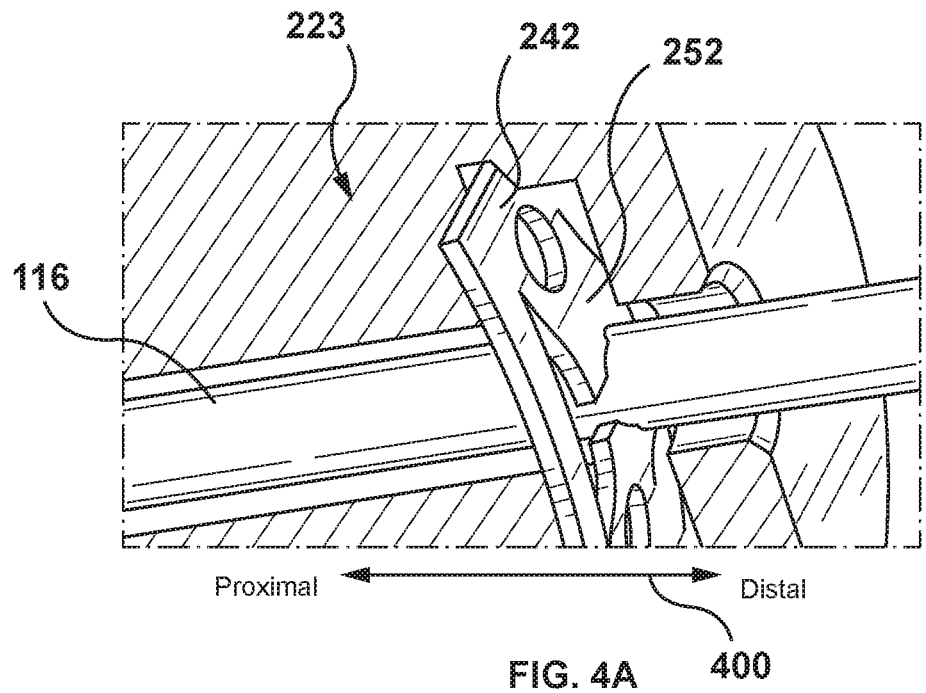
FIG. 4A is a magnified perspective view of a portion of FIG. 3A.

With continued reference to FIG. 3A and further reference to FIG. 4A, the delivery system 100 also includes a distal pusher shaft anchor 223 that is mechanically couplable to the pusher shaft 116 via a distal pusher shaft stop 242 (illustrated in detail in FIG. 4A). The distal pusher shaft anchor 223 is disposed within the housing 110. The distal pusher shaft stop 242 is a generally planar component that is disposed within the distal pusher shaft anchor 223 as best illustrated in the close-up view of FIG. 4A. The distal pusher shaft anchor 223 includes distal pusher shaft anchor threads 224 which are arranged on thread extensions 226 thereof. The distal pusher shaft anchor 223 is shaped and sized so as to fit inside housing 110. In the embodiment depicted in FIG. 3A, the distal pusher shaft anchor 223 is generally tubular or cylindrical with thread extensions 226 radially extending from opposing sides thereof as tabs. The distal pusher shaft anchor 223, as well as the distal pusher shaft stop 242, each include a central hole to permit the passage of the pusher shaft 116, the central shaft 112, and any other necessary components.

As stated above, the distal pusher shaft anchor 223 is mechanically couplable to the pusher shaft 116 via the distal pusher shaft stop 242. More particularly, depending on a direction of movement of the pusher shaft 116 with respect to the distal pusher shaft anchor 223, the distal pusher shaft anchor 223 may mechanically engage the pusher shaft 116 to prevent movement of the pusher shaft 116 with respect to the distal pusher shaft anchor 223 or may permit movement of the pusher shaft 116 with respect to the distal pusher shaft anchor 223 as will be described in more detail herein. Stated another way, the distal pusher shaft stop 242 acts as a one-way mechanical stop, permitting the pusher shaft 116 to move in one direction but not the other. The distal pusher shaft stop 242 has distal pusher shaft stop engagement tabs 252 integrally formed thereon as best illustrated in the close-up view of FIG. 4A. The distal pusher shaft stop 242 is configured to mechanically engage and secure the pusher shaft 116 via engagement tabs 252 when the distal pusher shaft stop 242 is moved proximally with respect to the pusher shaft 116. Thus, if force is applied to the pusher shaft 116 in a proximal direction (as shown by a directional arrow 400), mechanical engagement between the engagement tabs 252 and the pusher shaft 116 prevents proximal axial movement of the pusher shaft 116. More particularly, when force is applied to the pusher shaft 116 in the proximal direction, engagement between the pusher shaft 116 and the engagement tabs 252 causes the engagement tabs 252 to flex inward and tighten the mechanical connection with the pusher shaft 116. Thus, the distal pusher shaft stop 242 is configured to prevent proximal movement of the pusher shaft 116 with respect to the distal pusher shaft stop 242. Conversely, the distal pusher shaft stop 242 is configured to permit distal movement of the pusher shaft 116 with respect to the distal pusher shaft stop 242. When force is applied to the pusher shaft 116 in a distal direction (as shown by the directional arrow 400), the engagement tabs 252 flex outward and loosen the mechanical connection with the pusher shaft 116, thus permitting its passage.

Figure 4B:
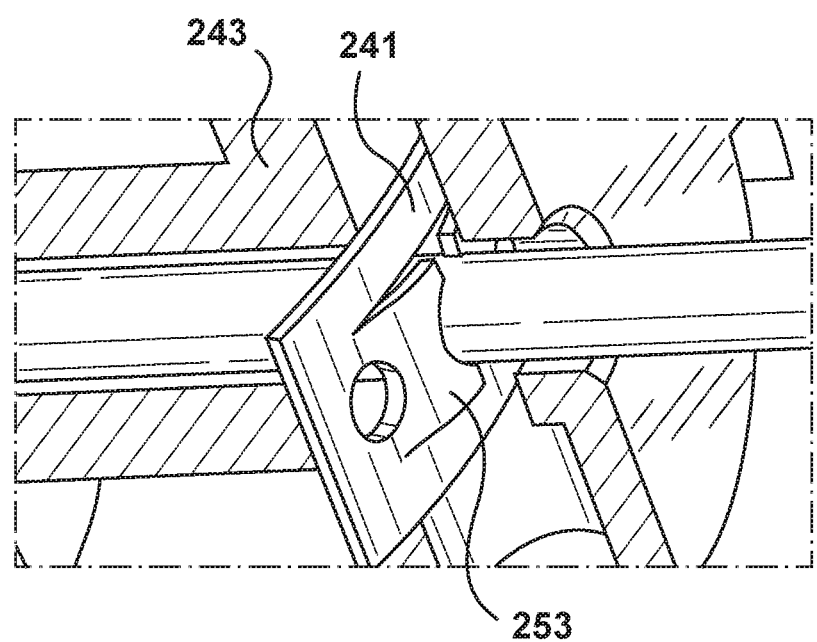
FIG. 4B is a magnified perspective view of a portion of FIG. 3A.

With continued reference to FIG. 3A and further reference to FIG. 4B, the delivery system 100 also includes a proximal pusher shaft anchor 243 including a proximal pusher shaft stop 241 which is mechanically couplable to the pusher shaft 116. The proximal pusher shaft anchor 243 is disposed within the housing 110. The proximal pusher shaft stop 241 is a generally planar component that is disposed within the proximal pusher shaft anchor 243 as best illustrated in the close-up view of FIG. 4B. The proximal pusher shaft stop 241 acts as a one-way mechanical stop, similarly to the distal pusher shaft stop 242. More particularly, FIG. 4B illustrates a close-up view of the proximal pusher shaft anchor 243 and the proximal pusher shaft stop 241 having proximal pusher shaft stop engagement tabs 253 integrally formed thereon. The proximal pusher shaft stop 241 and the engagement tabs 253 are configured to permit distal movement of the pusher shaft 116 while preventing proximal movement of the pusher shaft 116 and operate in the same fashion as the distal pusher shaft stop 242 and the engagement tabs 252. The proximal pusher shaft anchor 243 may be integral with or set within the housing 110 so as to be substantially immobile within the housing 110. Stated another way, the proximal pusher shaft anchor 243 is mechanically attached to interior walls of the housing 110 and is configured to remain stationary inside the housing 110 when subject to axial forces.

FIGS. 4A and 4B illustrate example embodiments of the proximal pusher shaft stop 241 and the distal pusher shaft stop 242. The proximal pusher shaft stop 241 and the distal pusher shaft stop 242 are each configured to permit one-way passage of the pusher shaft 116. The illustrated design, including the engagement tabs 252 and the engagement tabs 253, is illustrative only, and a person of skill in the art may recognize multiple alternative mechanical structures that may permit one-way passage of the pusher shaft 116, including, e.g., cam systems, cone systems, ratchet systems, and other mechanical one-way engagements.

With each of the outer sheath anchor 221, the distal pusher shaft anchor 223, and the proximal pusher shaft anchor 243 structurally described above, components of the single action deployment assembly 302 will now be introduced. The single action deployment assembly 302 includes the single action deployment ring 107 and a single action threaded carriage 320 that is integral with and/or mechanically coupled to the single action deployment ring 107. The single action threaded carriage 320 is also integral with and/or mechanically coupled to the grip barrel 108. The single action threaded carriage 320 includes single action threads 321 located on an interior wall thereof and an engagement surface 325. The single action threads 321 are configured to engage the housing threads 111 of the housing 110. The engagement surface 325 is positioned so as to engage or abut against the dual action threaded carriage 202 when the single action threaded carriage 320 is translated in a proximal direction.

When the single action deployment ring 107 and the single action threaded carriage 320 attached thereto rotates, the single action threads 321 of the single action threaded carriage 320 engage the housing threads 111 of the housing 110. The engagement between the housing threads 111 and the single action threads 321 generates relative linear movement between the single action threaded carriage 320 and the housing 110 when the single action threaded carriage 320 is rotated. The relative linear movement causes the single action threaded carriage 320 to translate either proximally or distally with respect to the housing 110, depending on a direction of rotation of the single action deployment ring 107.

The components of the dual action deployment assembly 301 will now be introduced. The dual action deployment assembly 301 includes the dual action deployment ring 109 and a dual action threaded carriage 202 that is integral with and/or mechanically coupled to the dual action deployment ring 109. The dual action threaded carriage 202 is a tubular structure provided with a threaded interior wall that is arranged so as to engage the threads of the distal pusher shaft anchor 223 and the threads of the outer sheath anchor 221. More particularly, the threaded interior wall of the dual action threaded carriage includes a proximal set of dual action threads 204 and a distal set of dual action threads 205, with the proximal set of dual action threads 204 arranged proximally to the distal set of dual action threads 205. The proximal set of dual action threads 204 is positioned to engage the distal pusher shaft anchor threads 224 of the distal pusher shaft anchor 223 through two opposing slots 305 (best shown in FIG. 3B, in which only one of the two opposing slots 305 is visible) of the housing 110. The distal set of dual action threads 205 is positioned to engage the outer sheath anchor threads 222 of the outer sheath anchor 221 through the opposing slots 305 of the housing 110. Each slot 305 is a slot, channel, gap, window, or opening formed in or through a sidewall of the housing 110. The respective threads of the distal pusher shaft anchor 223 and the outer sheath anchor 222 are positioned on the thread extensions 226 which extend therefrom. The thread extensions 226 extend or are positioned through the opposing slots 305 of the housing 110 so as to prevent the outer sheath anchor threads 222 and the distal pusher shaft anchor threads 224 for engagement by the threads of the dual action threaded carriage 202. Stated another way, the walls of each slot 305 are disposed adjacent to each side of the thread extensions 226 to prevent rotation of the outer sheath anchor 221 and the distal pusher shaft anchor 223.

Notably, the outer sheath anchor threads 222 are opposingly pitched (i.e., having a different handedness) to the distal pusher shaft anchor threads 224, while the proximal dual action threads 204 and the distal dual action threads 205 of the dual action threaded carriage 202 are pitched in the same direction as each other. The opposing pitch engagement contributes to the operation of the dual action deployment assembly 301 as will be described in more detail herein. In another embodiment, the outer sheath anchor threads 222 may be pitched in a same direction as the distal pusher shaft anchor threads 224 while the proximal dual action threads 204 and the distal dual action threads 205 are opposingly pitched. Thus, the pitch engagement of the outer sheath anchor threads 222 with the distal dual action threads 205 opposes the pitch engagement of the distal pusher shaft anchor threads 224 with the proximal dual action threads 204.

When the dual action deployment ring 109 is rotated, the dual action thread carriage 202 rotates therewith. When rotated, the dual action deployment ring 109 and the dual action threaded carriage 202 attached thereto do not axially move due to the grip barrel 108. Stated another way, the dual action deployment ring 109 and the dual action threaded carriage 202 are prevented from linear translation relative to the housing 110 via mechanical engagement with the grip barrel 108. More particularly, as previously described, the grip barrel 108 is integral with the single action threaded carriage 320 which includes single action threads 321 located on an interior wall thereof. Single action threads 321 engage or mate with the housing threads 111 of the housing 110. Due to the engagement between single action threads 321 and housing threads 111, the grip barrel 108 cannot axially move or translate unless it is rotated. Thus, when the dual action deployment ring 109 and the dual action threaded carriage 202 attached thereto are rotated, the dual action deployment ring 109 and the dual action threaded carriage 202 spin without translating or moving axially because the dual action deployment ring 109 abuts against the non-moving grip barrel 108. In another embodiment, the dual action deployment ring 109 and the dual action threaded carriage 202 are not prevented from linear translation via engagement with the grip barrel 108 but rather the opposing force engagement with the distal pusher shaft anchor 223 and the outer sheath anchor 221 (i.e., the opposing pitches of the outer sheath anchor threads 222 and the distal pusher shaft anchor threads 224) is relied upon to prevent linear translation of the dual action deployment ring 109.

When the dual action deployment ring 109 and the dual action thread carriage 202 rotate, the thread engagement between the threads of the dual action threaded carriage 202 and the threads of the distal pusher shaft anchor 223, and the thread engagement between the threads of the dual action threaded carriage 202 and the threads of the outer sheath anchor 221, cause axial movement or translation of the distal pusher shaft anchor 223 and the outer sheath anchor 221 in opposing directions. More particularly, when the dual action deployment ring 109 and the dual action thread carriage 202 rotate, the distal pusher shaft anchor threads 224 of the distal pusher shaft anchor 223 and the proximal dual action threads 204 of the dual action threaded carriage 202 engage and result or cause linear or axial movement or translation of the distal pusher shaft anchor 223. Threads 224, 204 are used to convert rotational to translational or linear movement. More particularly, because the distal pusher shaft anchor 223 is prevented from rotating relative to the housing 110 as explained above due to the walls of the slots 305, and because the dual action deployment ring 109 and the dual action threaded carriage 202 do not axially move due to the grip barrel 108, the rotational movement of the dual action deployment ring 109 and the dual action thread carriage 202 is converted to translational or linear movement of the distal pusher shaft anchor 223 in a distal direction due to the threaded relationship between the distal pusher shaft anchor 223 and the dual action threaded carriage 202.

Further, when the dual action deployment ring 109 and the dual action thread carriage 202 rotate, the outer sheath anchor threads 222 of the outer sheath anchor 221 and the distal dual action threads 205 of the dual action threaded carriage 202 engage and result or cause linear or axial movement or translation of the outer sheath anchor 221 in an opposing direction as the distal pusher shaft anchor 223. Threads 222, 205 are used to convert rotational to translational or linear movement. More particularly, because the outer sheath anchor 221 is prevented from rotating relative to the housing 110 as explained above due to the walls of the slots 305, and because the dual action deployment ring 109 and the dual action threaded carriage 202 do not axially move due to the grip barrel 108, the rotational movement of the dual action deployment ring 109 and the dual action thread carriage 202 is converted to translational or linear movement of the outer sheath anchor 221 in a proximal direction due to the threaded relationship between the distal pusher shaft anchor 223 and the dual action threaded carriage 202. The opposing pitch engagement between the threads of the dual action threaded carriage 202 and the threads of the distal pusher shaft anchor 223 and the outer sheath anchor 221 cause the distal pusher shaft anchor 223 and the outer sheath anchor 221 to translate axially in opposing directions.

The engaged threads may include different pitches so that the distal pusher shaft anchor 223 and the outer sheath anchor 221 move at different rates. More particularly, for example, the outer sheath anchor threads 222 and the distal dual action threads 205 may have a first pitch while the distal pusher shaft anchor threads 224 and the proximal dual action threads 204 may have a second, different pitch. In this example, rotation of the dual action deployment ring 109 causes axial translation of the distal pusher shaft anchor 223 and the outer sheath anchor 221 at different rates. In another embodiment hereof, the engaged threads may include different pitches but not opposing pitch directions. Accordingly, in such an example, rotation of the dual action deployment ring 109 causes axial translation of the distal pusher shaft anchor 223 and the outer sheath anchor 221 in the same direction but at different rates.

With the structural components introduced, the operation of the dual action deployment assembly 301 and the single action deployment assembly 302 will now be described. More particularly, the operation of the dual action deployment assembly 301 will first be described in more detail with reference to FIG. 5A. As discussed above, the dual action deployment assembly 301 is configured to provide axial translation of the outer sheath 104 and the pusher shaft 116 in opposing directions. With the dual action deployment assembly 301, deployment of a prosthesis (such as the prosthesis 101) is accomplished at the accelerated or faster rate (relative to a standard rate accomplished by the single action deployment assembly 302) by advancing the pusher shaft 116 simultaneous to the retraction of the outer sheath 104. That is, the pusher shaft 116 acts to push the prosthesis 101 distally rather than acting only as a stop to prevent the prosthesis 101 from movement in a proximal direction as the sheath is retracted.

Figure 5A:
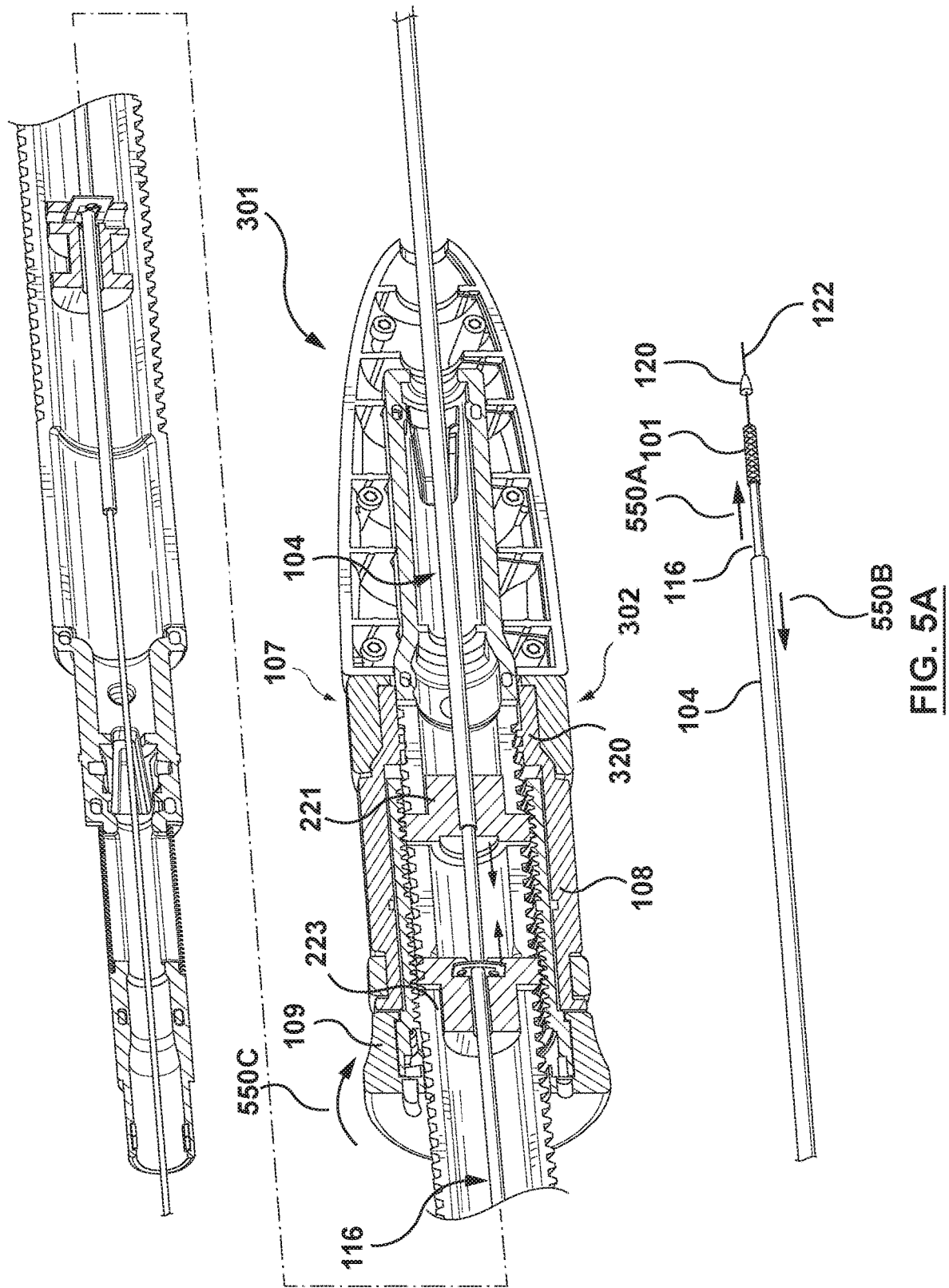
FIG. 5A illustrates operation of the dual action deployment mechanism of the prosthesis delivery system of FIG. 1A.

More particularly, with reference to FIG. 5A, the dual action deployment ring 109 and the dual action thread carriage 202 are rotated in a first direction (represented by arrow 550C) to cause the distal pusher shaft anchor 223 to translate distally as represented by a directional arrow 550A and the outer sheath anchor 221 to translate proximally as represented by a directional arrow 550B. Movement of the outer sheath anchor 221 in a proximal direction as represented by the directional arrow 550B causes the outer sheath 104 fixed thereto to move with it. Movement of the distal pusher shaft anchor 223 in a distal direction as represented by the directional arrow 550A causes the engagement tabs 252 of the distal pusher shaft stop 242 to engage the pusher shaft 116 and distally advance the pusher shaft 116 as the distal pusher shaft anchor 223 is distally advanced. Thus, rotation of the dual action deployment ring 109 and the dual action thread carriage 202 causes the outer sheath 104 to retract proximally with respect to the housing 110 while simultaneously causing the pusher shaft 116 to advance distally with respect to the housing 110. Because the pusher shaft 116 is moving distally with respect to the proximal pusher shaft anchor 243 and proximal pusher shaft stop 241, the engagement tabs 253 of the proximal pusher shaft stop 241 permit passage of the pusher shaft 116.

The operation of the single action deployment assembly 302 will now be described in more detail with reference to FIG. 5B. As discussed above, the single action deployment assembly 302 is configured to provide axial translation of the outer sheath 104 while maintaining the pusher shaft 116 in a stationary position. Stated another way, the single action deployment mechanism 302 is configured to retract the outer sheath 104 without advancing the pusher shaft 116. Accordingly, when operated, the single action deployment mechanism 302 delivers a prosthesis (such as prosthesis 101) to the treatment site at a slower rate than the dual action deployment mechanism 301.

Figure 5B:
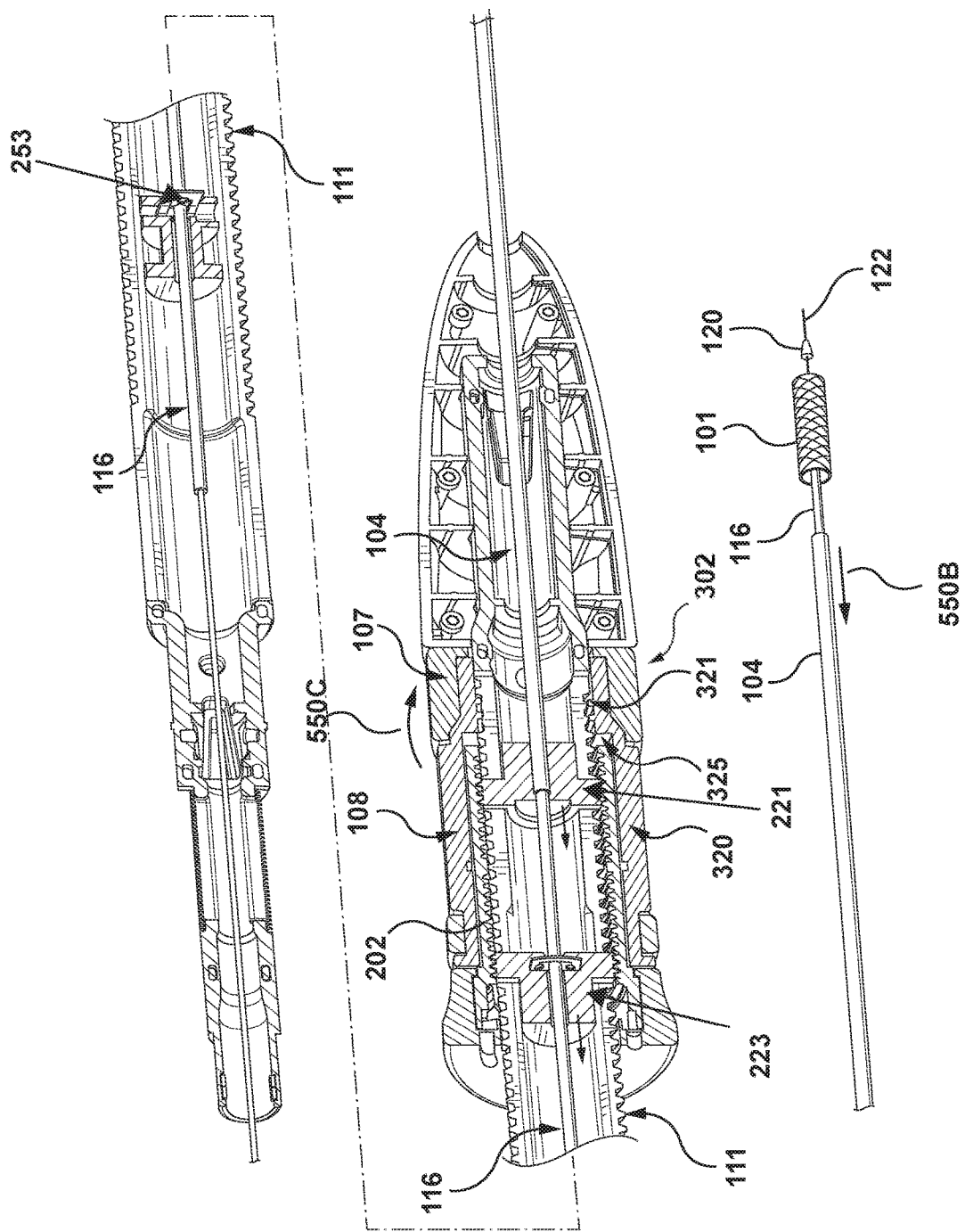
FIG. 5B illustrates operation of the single action deployment mechanism of the prosthesis delivery system of FIG. 1A.

More particularly, as illustrated in FIG. 5B, the single action deployment ring 107 and the single action threaded carriage 320 attached thereto are rotated in a first direction (represented by arrow 550C) so as to cause the single action threaded carriage 320 to translate in a proximal direction as represented by the directional arrow 550B. The engagement surface 325 of the single action threaded carriage 320 contacts or abuts against the dual action threaded carriage 202 and thus the dual action threaded carriage 202 is forced to translate proximally as well. Proximal translation of the dual action threaded carriage 202 also causes the proximal translation of both the outer sheath anchor 221 and the distal pusher shaft anchor 223 via the non-rotational engagement between the threads of the dual action threaded carriage 202 and those of the outer sheath anchor 221 and the distal pusher shaft anchor 223. Proximal translation of the outer sheath anchor 221 causes the outer sheath 104 to retract. Proximal translation of the distal pusher shaft anchor 223, however, does not result in proximal axial translation of the pusher shaft 116. In this operation of the single action deployment ring 107, the proximal movement of the distal pusher shaft anchor 223 with respect to the pusher shaft 116 can be understood as comparable to distal movement of the pusher shaft 116 with respect to the distal pusher shaft anchor 223. As the distal pusher shaft anchor 223 moves proximally, the proximal engagement tabs 253 of the proximal pusher shaft stop 241 maintain the position of the pusher shaft 116 relative to the handle 102 such that the distal engagement tabs 252 of the distal pusher shaft stop 242 do not engage the pusher shaft 116 and allow the distal pusher shaft anchor 223 to move proximally relative to the pusher shaft 116.

With the operations of the dual action deployment assembly 301 and the single action deployment assembly 302 fully described, it is also notable to describe the effects of rotating both the dual action deployment ring 109 and the single action deployment ring 107 in a reverse or second direction opposite the first direction. When rotated in a second or reverse direction, opposite from the directional arrow 550C, the dual action deployment ring 109 causes the outer sheath anchor 221 to undergo axial movement or translation in a distal direction as represented by the directional arrow 550A. Movement of the outer sheath anchor 221 in a distal direction as represented by the directional arrow 550A causes the outer sheath 104 fixed thereto to move with it. Such movement, wherein the outer sheath 104 is advanced relative to the pusher shaft 116, may be employed to return outer sheath 104 to its original position to permit smooth withdrawal of the tip 120 without catching on the vasculature. Rotation of the dual action deployment ring 109 in the second or opposing direction also causes the distal pusher shaft anchor 223 to translate in a proximal axial direction as represented by the directional arrow 550B. However, proximal axial translation of the distal pusher shaft anchor 223 does not result in proximal axial translation of the pusher shaft 116. In this operation of the dual action deployment ring 109, similar to the operation described above with respect to the rotation of the single action deployment ring 107 rotated in a first direction represented by arrow 550C, the proximal movement of the distal pusher shaft anchor 223 with respect to the pusher shaft 116 can be understood as comparable to distal movement of the pusher shaft 116 with respect to the distal pusher shaft anchor 223. As the distal pusher shaft anchor 223 moves proximally, the proximal engagement tabs 253 of the proximal pusher shaft stop 241 maintain the position of the pusher shaft 116 relative to the handle 102 such that the distal engagement tabs 252 of the distal pusher shaft anchor 223 do not engage the pusher shaft 116 and allow the distal pusher shaft anchor 223 to move proximally relative to the pusher shaft 116.

When the single action deployment ring 107 is rotated in a second or reverse direction opposite from the directional arrow 550C, the single action threaded carriage 320 translates distally, the engagement surface 325 disengages from the dual action threaded carriage 202 and the dual action threaded carriage 202 remains stationary. In another embodiment hereof, the engagement surface 325 of the single action threaded carriage 320 may be configured to couple to a surface of the dual action threaded carriage 202 such that when the single action deployment ring 107 is rotated so as to cause the single action threaded carriage 320 to translate distally, dual action threaded carriage 202, the outer sheath anchor 221 and the distal pusher shaft anchor 223 also simultaneously or collectively translate distally. In this embodiment, distal movement or translation of the single action threaded carriage 320 causes distal movement or translation of the outer sheath 104 as well as distal movement or translation of the pusher shaft 116.

The dual action deployment assembly 301 and the single action deployment assembly 302 described above may be utilized to deploy portions of a single prosthesis at varying or differing rates to achieve differing structural results within the prosthesis. Operation of the dual action deployment assembly 301 deploys a prosthesis at an accelerated rate as compared to the single action deployment assembly 302. More particularly, during retraction of the outer sheath 104, friction between the outer sheath 104 and the prosthesis 101 creates axial compression of the stent structure of the prosthesis 101. Axial compression of the stent structure or framework of the prosthesis 101 is increased by the accelerated deployment rate, provided by the simultaneous advancement of the pusher shaft 116 and retraction of the outer sheath 104 of the dual action deployment mechanism 301. Stated another way, the accelerated deployment rate induces greater axial compression in the prosthesis due to the relative movement between the pusher shaft 116 and the prosthesis 101 in one direction and the outer sheath 104 in an opposite direction. Friction between the prosthesis 101 and the walls of the outer sheath 104 as these components move in opposite directions induces compression in the prosthesis. This compression is increased by the increased rate of relative movement between the prosthesis 101 and the walls of the outer sheath 104. Increased compression, in turn, leads to a greater density in stent structure in areas of the prosthesis 101 deployed under the accelerated deployment rate. This greater density of the stent structure or framework causes a higher radial force in these areas. When the prosthesis 101 is deployed, those portions of the prosthesis 101 with increased axial compression produce or exert a greater radial force, for example, because the stent structural materials are concentrated due to the axial compression as shown and described below with respect to FIGS. 6A and 6B. The increased radial force is present during deployment, as the prosthesis 101 expands into a deployed position. The increased radial force remains present after deployment, as the compressed portions of the prosthesis 101 continue to exert increased radial force on the surrounding anatomy.

FIGS. 6A and 6B illustrate varying prosthesis configurations as deployed by single action and dual action mechanisms described herein. FIG. 6A illustrates a stent-graft 601A having a portion thereof deployed at an accelerated rate with the delivery system 100. More particularly, the dual action deployment assembly 301 is used to deploy the stent-graft 601A at an accelerated deployment rate for at least a portion of the deployment, thereby producing an area of increased compression 610. A remainder of the deployment is performed via the single action deployment assembly 302, thereby resulting in a remainder of the prosthesis 601A being deployed with standard compression. Although the area of increased compression 610 is shown along a midportion of the prosthesis 601A, this is only exemplary. It will be understood by one of ordinary skill in the art that the area of increased compression 610 may be positioned at other locations along a length of the prosthesis 601A, such as but not limited to one or more end portions of the prosthesis 601A. In addition, although the prosthesis 601A is shown with only a single area of increased compression 610, this is also only exemplary, and it will be understood by one of ordinary skill in the art that the prosthesis 601A may include a plurality of areas of increased compression 610. The delivery system 100 described herein permits an operator to alternate between single action and dual action deployment assemblies as desired, thus allowing the deployment of a prosthesis with discrete zones of high and low compression in the stent structure (and correspondingly increased and decreased radial forces). Increased radial forces resulting from the area of increased compression 610 may be desirable in specific applications, including, but not limited to, deployment within areas of high plaque in the vasculature and/or at anchor points of the prosthesis structure. Decreased or standard radial forces are desirable when such increased radial forces are not deemed necessary, because standard radial forces limit or minimize vascular interaction with the deployed prosthesis.

Further, if an area of increased compression and the resulting increased radial force therefrom is not required, an operator may also select to operate the delivery system 100 entirely in a single action mode, leading to a slower deployment and reduced relative movement between the prosthesis and the interior wall of the outer sheath 104 during deployment. Slower deployment leads to less compression in the stent structure and a uniform distribution of stent structure members across a length of a prosthesis, as shown in FIG. 6B which illustrates a stent-graft 601B deployed with standard compression and therefore having no areas of increased compression. Rather, the stent structure of stent-graft 601B has a uniform distribution along a length of the stent-graft.

Although FIGS. 6A and 6B illustrate prostheses having helical support structures, this is by way of example only. The systems, devices, and methods described herein are not limited to stents or prostheses having helical support structures. Differing stent support structures, such as those having individual rings, may equally be employed with the invention.

Figure 7:
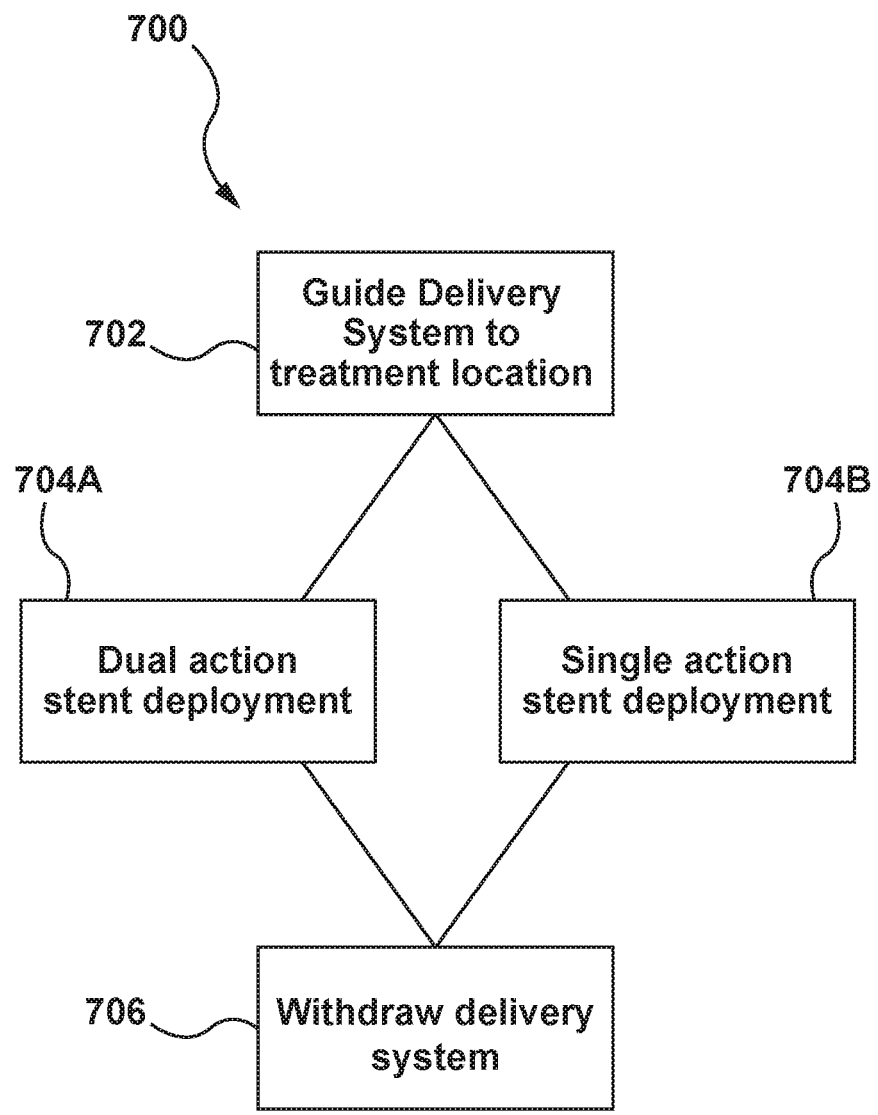
FIG. 7 is a flow chart showing operations of an illustrative method according to aspects of this disclosure.

FIG. 7 is a flow chart of a method 700 of dual action deployment of a prosthesis. In an operation 702, a prosthesis delivery system is manipulated to navigate a prosthesis delivery catheter tip to a prosthesis deployment site. The prosthesis delivery system is navigated through a procedural catheter, a guide catheter, and/or an introducer catheter to deliver a prosthesis contained within the prosthesis delivery system to a site for deployment of the prosthesis. In some embodiments, the prosthesis delivery system may be delivered via a guidewire that has previously been inserted into the patient vasculature.

In an operation 704A, 704B, at least one deployment mechanism of the prosthesis delivery system is operated. When an operator has confirmed that the prosthesis containing tip of the catheter has been appropriately positioned with the vasculature system of the patient, the prosthesis may be deployed.

For example, at the operation 704A, a dual action deployment mechanism of a prosthesis delivery system is manipulated to cause prosthesis deployment. Operation of the dual action deployment mechanism causes the proximal retraction of an outer sheath covering the prosthesis and the simultaneous distal advancement of a pusher shaft member configured to engage the prosthesis. Operation of the dual action deployment mechanism retracts the outer sheath of the prosthesis delivery system, thereby exposing the prosthesis. At the same time, due to operation of the dual action deployment system, the pusher shaft is advanced and pushes the prosthesis forward. The simultaneous distal advancement of the pusher shaft and proximal retraction of the outer sheath causes the rapid deployment of the prosthesis. Due to the relative movement between the interior wall of the outer sheath and the prosthesis, the prosthesis is axially compressed during deployment and thus exhibits increased radial force at areas of such increased axial compression.

An operator of the prosthesis delivery system may also employ a single action deployment mechanism to deploy a prosthesis, as shown in the operation 704B. Operation of the single action deployment mechanism causes the outer sheath to proximally retract and the pusher shaft to remain stationary. The pusher shaft exerts force on the prosthesis, or acts as a stopper, to prevent the prosthesis from retracting with the outer sheath. Operation of the single action deployment mechanism causes deployment of the prosthesis at a rate slower than that of the dual action deployment mechanism. Further, operation of the single action deployment mechanism does not result in the prosthesis being axially compressed and exhibiting increased radial force at areas of such increased axial compression as described above with respect to the dial action deployment mechanism.

The operator may, in some examples, select to employ both the dual action and single action deployment mechanisms, thereby causing deployment of the prosthesis at varying rates, thus controlling variable amounts of compression along the length of the deployed prosthesis (and corresponding variable radial forces along the length of the deployed prosthesis).

In an operation 706, an operator withdraws the prosthesis delivery system after deployment of the prosthesis is complete.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A prosthesis delivery device comprising:
a housing;
an outer sheath including a proximal portion mechanically coupled to a sheath anchor within the housing;
a pusher shaft having a distal portion disposed inside of the outer sheath and a proximal portion mechanically coupled to a pusher shaft anchor within the housing;
a central shaft having a proximal portion and a distal portion disposed inside of the pusher shaft;
a first deployment assembly located exterior to the housing and configured to simultaneously advance the outer sheath and the pusher shaft in opposing axial directions; and
a second deployment assembly located exterior to the housing configured to retract the outer sheath while maintaining the pusher shaft stationary relative to the housing, wherein the second deployment assembly includes a second deployment ring having second deployment ring internal threads configured to engage external threads of the housing and being configured for axial translation along the housing and to retract the outer sheath while maintaining the pusher shaft stationary relative to the housing.

2. The device of claim 1, wherein:
the first deployment assembly comprises a first deployment ring including a first set of internal threads and a second set of internal threads,
the pusher shaft anchor includes pusher shaft anchor threads configured to engage the first set of internal threads through a slot in the housing,
the sheath anchor includes sheath anchor threads configured to engage the second set of internal threads through the slot in the housing, and
the first deployment assembly is configured to simultaneously advance the outer sheath and the pusher shaft in opposing axial directions when the first deployment ring is rotated relative to the housing.

3. The device of claim 2, wherein the first set of internal threads and the second set of internal threads include opposite pitch directions.

4. The device of claim 2, wherein the sheath anchor threads and the pusher shaft anchor threads include opposite pitch directions.

5. The device of claim 1, further comprising:
a first pusher shaft stop mechanically coupled to the pusher shaft anchor; and
a second pusher shaft stop mechanically coupled to the housing,
wherein the first pusher shaft stop permits axial movement of the pusher shaft relative to the first pusher shaft stop in a distal direction and prevents axial movement of the pusher shaft relative to the first pusher shaft stop in a proximal direction, and the second pusher shaft stop permits axial movement of the pusher shaft relative to the first pusher shaft stop in the distal direction and prevents axial movement of the pusher shaft relative to the first pusher shaft stop in the proximal direction.

6. The device of claim 5, wherein operation of the first deployment assembly causes mechanical engagement between the first pusher shaft stop and the pusher shaft, maintaining relative positions between the first pusher shaft stop and the pusher shaft and permitting relative movement between the second pusher shaft stop and the pusher shaft.

7. The device of claim 5, wherein operation of the second deployment assembly causes mechanical engagement between the second pusher shaft stop and the pusher shaft, maintaining relative positions between the second pusher shaft stop and the pusher shaft and permitting relative movement between the pusher shaft and the first pusher shaft stop.

8. The device of claim 1, wherein operation of the first deployment assembly is configured to cause compression of a prosthesis to be deployed through relative movement between the sheath and the pusher shaft.

9. A prosthesis delivery system comprising:
a prosthesis configured for delivery to vasculature of a subject;
a housing;
an outer sheath including a proximal portion mechanically coupled to a sheath anchor within the housing;
a pusher shaft having a distal portion disposed inside of the outer sheath and a proximal portion mechanically coupled to a pusher shaft anchor within the housing;
a central shaft having a proximal portion and a distal portion disposed inside of the pusher shaft, the prosthesis being mounted on the distal portion of the central shaft;
a first deployment assembly located exterior to the housing and configured to simultaneously advance the outer sheath and the pusher shaft in opposing axial directions; and
a second deployment assembly located exterior to the housing configured to retract the outer sheath while maintaining the pusher shaft stationary relative to the housing, wherein the second deployment assembly includes a second deployment ring having second deployment ring internal threads configured to engage external threads of the housing and being configured for axial translation along the housing and to retract the outer sheath while maintaining the pusher shaft stationary relative to the housing.

10. The system of claim 9, wherein a distal end of the distal portion of the pusher shaft is configured to engage the prosthesis during prosthesis deployment.

11. The system of claim 9, further comprising:
a first pusher shaft stop mechanically coupled to the pusher shaft anchor; and
a second pusher shaft stop mechanically coupled to the housing,
wherein the first pusher shaft stop permits axial movement of the pusher shaft relative to the first pusher shaft stop in a distal direction and prevents axial movement of the pusher shaft relative to the first pusher shaft stop in a proximal direction, and the second pusher shaft stop permits axial movement of the pusher shaft relative to the first pusher shaft stop in the distal direction and prevents axial movement of the pusher shaft relative to the first pusher shaft stop in the proximal direction.

12. A prosthesis delivery device comprising:
a housing;
an outer sheath including a proximal portion mechanically coupled to a sheath anchor within the housing;
a pusher shaft having a distal portion disposed inside of the outer sheath and a proximal portion mechanically coupled to a pusher shaft anchor within the housing;
a central shaft having a proximal portion and a distal portion disposed inside of the pusher shaft;
a first deployment assembly located exterior to the housing and configured to simultaneously advance the outer sheath and the pusher shaft in opposing axial directions; and
a second deployment assembly located exterior to the housing configured to retract the outer sheath while maintaining the pusher shaft stationary relative to the housing,
a first pusher shaft stop mechanically coupled to the pusher shaft anchor; and
a second pusher shaft stop mechanically coupled to the housing,
wherein the first pusher shaft stop permits axial movement of the pusher shaft relative to the first pusher shaft stop in a distal direction and prevents axial movement of the pusher shaft relative to the first pusher shaft stop in a proximal direction, and the second pusher shaft stop permits axial movement of the pusher shaft relative to the first pusher shaft stop in the distal direction and prevents axial movement of the pusher shaft relative to the first pusher shaft stop in the proximal direction.

13. The device of claim 12, wherein operation of the first deployment assembly causes mechanical engagement between the first pusher shaft stop and the pusher shaft, maintaining relative positions between the first pusher shaft stop and the pusher shaft and permitting relative movement between the second pusher shaft stop and the pusher shaft.

14. The device of claim 12, wherein operation of the second deployment assembly causes mechanical engagement between the second pusher shaft stop and the pusher shaft, maintaining relative positions between the second pusher shaft stop and the pusher shaft and permitting relative movement between the pusher shaft and the first pusher shaft stop.

15. The device of claim 12, wherein:
the second deployment assembly comprises a second deployment ring including second deployment ring internal threads configured to engage external threads of the housing and is configured for axial translation along the housing and to retract the outer sheath while maintaining the pusher shaft stationary relative to the housing.

16. The device of claim 12, wherein:
the first deployment assembly comprises a first deployment ring including a first set of internal threads and a second set of internal threads,
the pusher shaft anchor includes pusher shaft anchor threads configured to engage the first set of internal threads through a slot in the housing,
the sheath anchor includes sheath anchor threads configured to engage the second set of internal threads through the slot in the housing, and
the first deployment assembly is configured to simultaneously advance the outer sheath and the pusher shaft in opposing axial directions when the first deployment ring is rotated relative to the housing.

17. The device of claim 12, further comprising a prosthesis configured for delivery to vasculature of a subject.

18. The device of claim 17, wherein the second deployment assembly includes a second deployment ring including second deployment ring internal threads configured to engage external threads of the housing and is configured for axial translation along the housing and to retract the outer sheath while maintaining the pusher shaft stationary relative to the housing.

19. The device of claim 17, wherein operation of the second deployment assembly causes mechanical engagement between the second pusher shaft stop and the pusher shaft, maintaining relative positions between the second pusher shaft stop and the pusher shaft and permitting relative movement between the pusher shaft and the first pusher shaft stop.

* * * * *